(12) United States Patent
Clements, IV et al.

(10) Patent No.: US 10,898,450 B2
(45) Date of Patent: Jan. 26, 2021

(54) MULTI-SEGMENTED TRANSDERMAL DOSING UNIT AND METHODS OF USE

(71) Applicant: Clemtech Pharmaceuticals, LLC, Pittsburgh, PA (US)

(72) Inventors: David Harrison Clements, IV, Philadelphia, PA (US); Eric D. Clements, Pittsburgh, PA (US)

(73) Assignee: Clemtech Pharmaceuticals, LLC, Pittsburgh, PA (US)

( * ) Notice: Subject to any disclaimer, the term of this patent is extended or adjusted under 35 U.S.C. 154(b) by 0 days.

(21) Appl. No.: 15/686,248

(22) Filed: Aug. 25, 2017

(65) Prior Publication Data

US 2018/0055784 A1 Mar. 1, 2018

Related U.S. Application Data

(60) Provisional application No. 62/379,408, filed on Aug. 25, 2016.

(51) Int. Cl.
*A61K 9/70* (2006.01)
*B32B 7/12* (2006.01)
*B32B 7/06* (2019.01)

(52) U.S. Cl.
CPC .......... *A61K 9/7092* (2013.01); *A61K 9/7061* (2013.01); *A61K 9/7069* (2013.01); *A61K 9/7084* (2013.01); *B32B 7/06* (2013.01); *B32B 7/12* (2013.01)

(58) Field of Classification Search
CPC ...... A61K 9/70; A61K 9/7007; A61K 9/7015; A61K 9/7023; A61K 9/7038; A61K 9/7046; A61K 9/7061; A61K 9/7084; A61K 9/7094
See application file for complete search history.

(56) References Cited

U.S. PATENT DOCUMENTS

| 6,221,384 B1* | 4/2001 | Pagedas | A61F 15/001 424/448 |
| 9,289,397 B2* | 3/2016 | Wright, IV | A61K 9/703 |
| 2001/0006628 A1* | 7/2001 | Govil | A61K 9/7061 424/78.31 |
| 2004/0265363 A1* | 12/2004 | Hille | A61K 9/7084 424/449 |
| 2015/0196515 A1* | 7/2015 | Aliyar | A61K 9/7084 604/307 |

* cited by examiner

*Primary Examiner* — Micah Paul Young
(74) *Attorney, Agent, or Firm* — Troutman Pepper Hamilton Sanders LLP

(57) ABSTRACT

A transdermal dosing unit may include a first segment having a first pharmaceutical in a first reservoir, a first releasing compound, and a first adhesive component, a second segment removably connected to the first segment, the second segment having a second pharmaceutical in a second reservoir, a second releasing component, and a second adhesive component, and a backing component. The transdermal dosing unit may further include additional segments, and may include a perforated section between each segment. The first adhesive component may have a first adhesion strength, and the second adhesive component may have a second adhesion strength that is either different from or approximately equal to the first adhesion strength. A method of titrating a dose of such a transdermal dosing unit may include applying the transdermal dosing unit to a subject, and removing the first segment while leaving the second segment on the subject.

22 Claims, 12 Drawing Sheets

MULTI-SEGMENTED TRANSDERMAL DOSING UNIT AND METHODS OF USE

CROSS-REFERENCE TO RELATED APPLICATIONS

This application claims priority to and benefit of U.S. Provisional Application Ser. No. 62/379,408, filed Aug. 25, 2016, entitled "Multi-Segmented Transdermal Dosing Unit and Methods of Use," which is hereby incorporated herein by reference in its entirety.

SUMMARY

Embodiments herein are directed to transdermal dosing units and methods of titrating a dose of a pharmaceutical product. In an embodiment, a transdermal dosing unit may comprise a first segment having a first pharmaceutical in a first reservoir, a first releasing component, and a first adhesive component, a second segment removably connected to the first segment, the second segment having a second pharmaceutical in a second reservoir, a second releasing component, and a second adhesive component, and a backing component. In some embodiments, the transdermal dosing unit may comprise one or more additional segments, each segment having a pharmaceutical, a reservoir, a releasing component, and a backing component, and each segment removably connected to at least one of the first and second segments. In further embodiments, the transdermal dosing unit may include one or more perforated sections between one or more of the segments. In certain embodiments, the first adhesive component may have a first adhesion strength, and the second adhesive component may have a second adhesion strength. In some embodiments, the first adhesion strength may differ from the second adhesion strength, while in other embodiments, the first adhesion strength may be approximately equal to the second adhesion strength.

In an embodiment, a method of titrating a dose of such a transdermal unit may include applying the transdermal dosing unit to a subject, and removing the first segment while leaving the second segment on the subject. In some embodiments, the first segment may be removed according to the symptoms of the subject. In certain embodiments, having a first adhesion strength different from the second adhesion strength may facilitate the removal of the first segment without disturbing the adhesion of the second segment to the subject.

DETAILED DESCRIPTION

Figure 1:
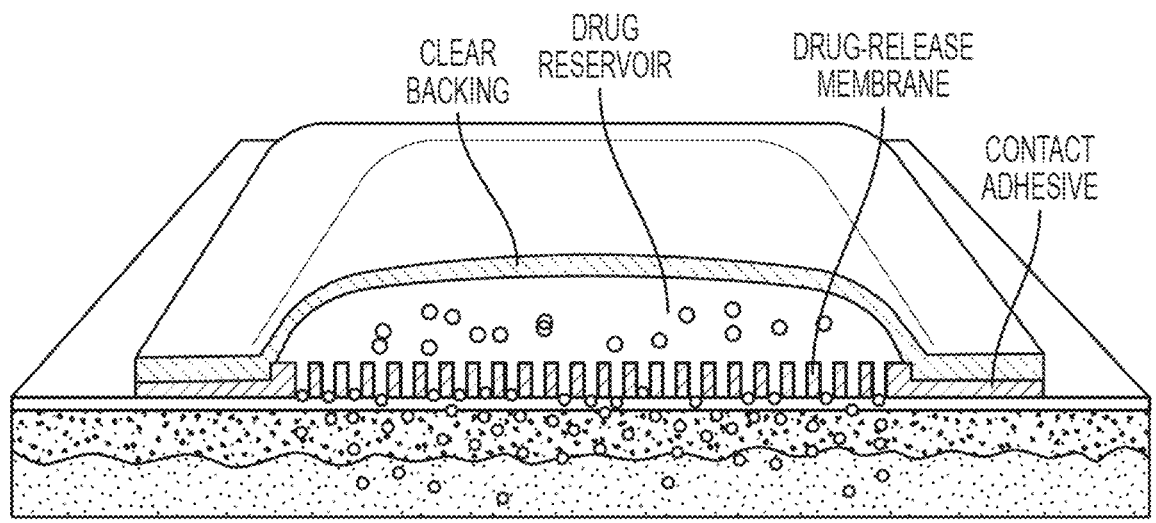
FIG. 1 illustrates a cross-sectional schematic diagram of an embodiment of segment of a transdermal dosing unit, in accordance with the present disclosure.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "pharmaceutical" is a reference to one or more pharmaceuticals and equivalents thereof known to those skilled in the art, and so forth.

As used herein, the term "about" means plus or minus 10% of the numerical value of the number with which it is being used. Therefore, about 50 mg means in the range of 45 mg to 55 mg.

In embodiments or claims where the term comprising is used as the transition phrase, such embodiments can also be envisioned with replacement of the term "comprising" with the terms "consisting of" or "consisting essentially of."

The term "subject," as used herein, includes but is not limited to humans and non-human vertebrates such as wild, domestic and farm animals. In some embodiments, the term "subject" may refer to humans.

As used herein, the phrase "pharmaceutically acceptable" means that the carrier, diluent, or excipient must be compatible with the other ingredients of the formulation or composition and not deleterious to the recipient thereof.

As used herein, the terms "treat," "treated," or "treating" refer to both therapeutic treatment and prophylactic or preventative measures, wherein the object is to prevent or slow down (lessen) an undesired physiological condition, disorder or disease, or to obtain beneficial or desired clinical results. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Transdermal dosing units have been developed to deliver a wide variety of pharmaceutical products through the skin. The primary advantage of such dosing units is that they provide a controlled release of a pharmaceutical to a subject. These dosing units, often in the form of patches, may also be useful for a subject who is unable to or would prefer not to receive a medication orally. Unlike oral medications, however, the dose of a transdermal dosing unit is difficult to adjust. A patch cannot be cut into portions as many oral medications can be, because severing the patch may change the way it releases its medication, rendering it unsafe and potentially useless to the subject. Still, though, a medical professional may prescribe a particular dosage unit for a subject, but the subject may find that the dose is too high or too low after he or she begins use. Under the medical professional's supervision, the subject may wish to adjust or titrate the dosage of the transdermal medication. In other cases, a medical professional may wish to administer more than one pharmaceutical at varying rates using a single transdermal dosing unit. Therefore, there exists a need for a multi-segmented transdermal dosing unit, each segment of which may be applied or removed from a subject as his or her symptoms dictate, or as his or her medical professional prescribes.

Transdermal Dosing Unit

In an embodiment, a transdermal dosing unit may comprise a first segment, a second segment removably connected to the first segment, and a backing component. The first segment may comprise a first pharmaceutical in a first reservoir, a first releasing component, and a first adhesive component. The second segment may comprise a second pharmaceutical in a second reservoir, a second releasing component, and a second adhesive component. In other embodiments, a transdermal dosing unit may further comprise one or more additional segments, each segment having its own pharmaceutical, reservoir, releasing component, and adhesive component. In such embodiments, the one or more additional segments may be removably connected to at least one of the first and second segments. In some embodiments, the transdermal dosing unit may comprise between two and eight total segments. The transdermal dosing unit may comprise, for example, a first segment, a second segment, a third segment, a fourth segment, a fifth segment, a sixth segment, a seventh segment, and/or an eighth segment, each segment independently having the components described above. The segments may be arranged in any configuration, including a linear configuration, a parallel configuration, or a concentric configuration. FIG. 1 illustrates a schematic diagram of a non-limiting embodiment of segment of a transdermal dosing unit, in accordance with the present disclosure.

In some embodiments, a transdermal dosing unit may further comprise one or more perforated sections between one or more of the segments. In such embodiments, the perforated sections may not contain a pharmaceutical, but may still comprise an adhesive, a filler, and a backing.

Figure 2:
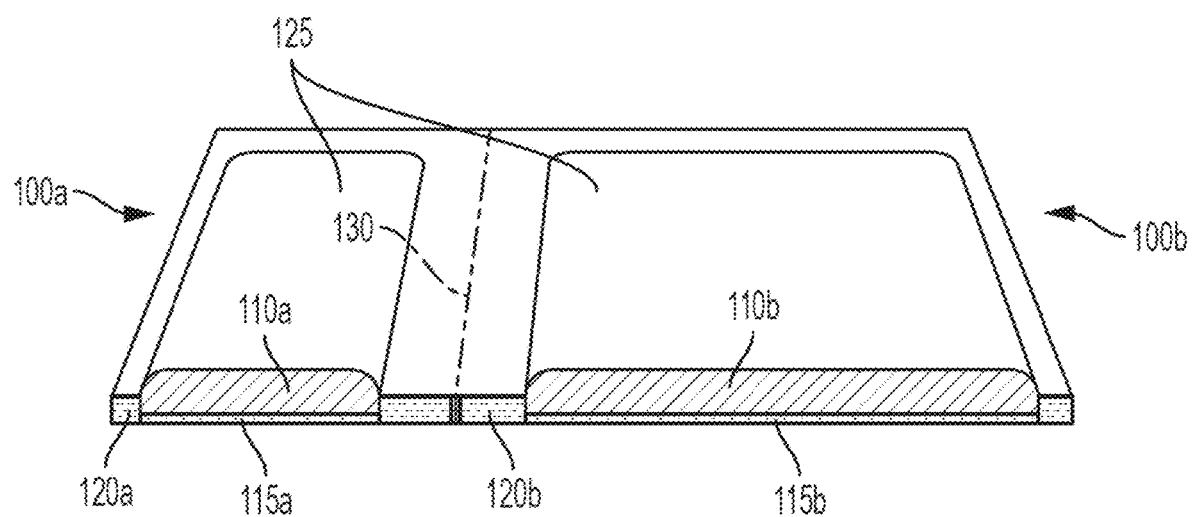
FIG. 2 illustrates an embodiment of a transdermal dosing unit in accordance with the present disclosure.
Figure 3A:
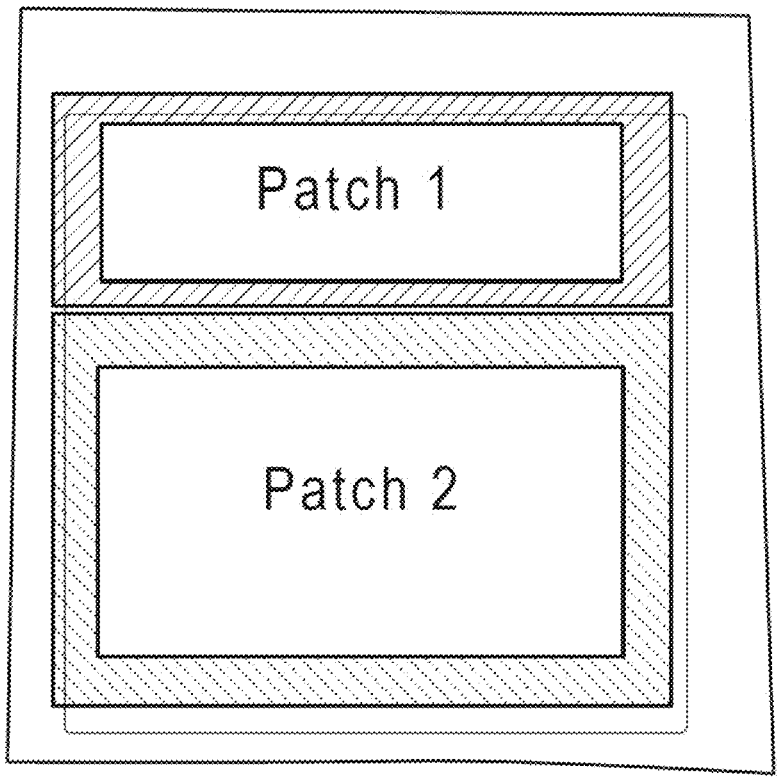
FIG. 3A illustrates a step of applying a transdermal dosing unit to a subject, in accordance with an embodiment of a method of titrating a dose of a transdermal dosing unit as described in the present disclosure.
Figure 3B:
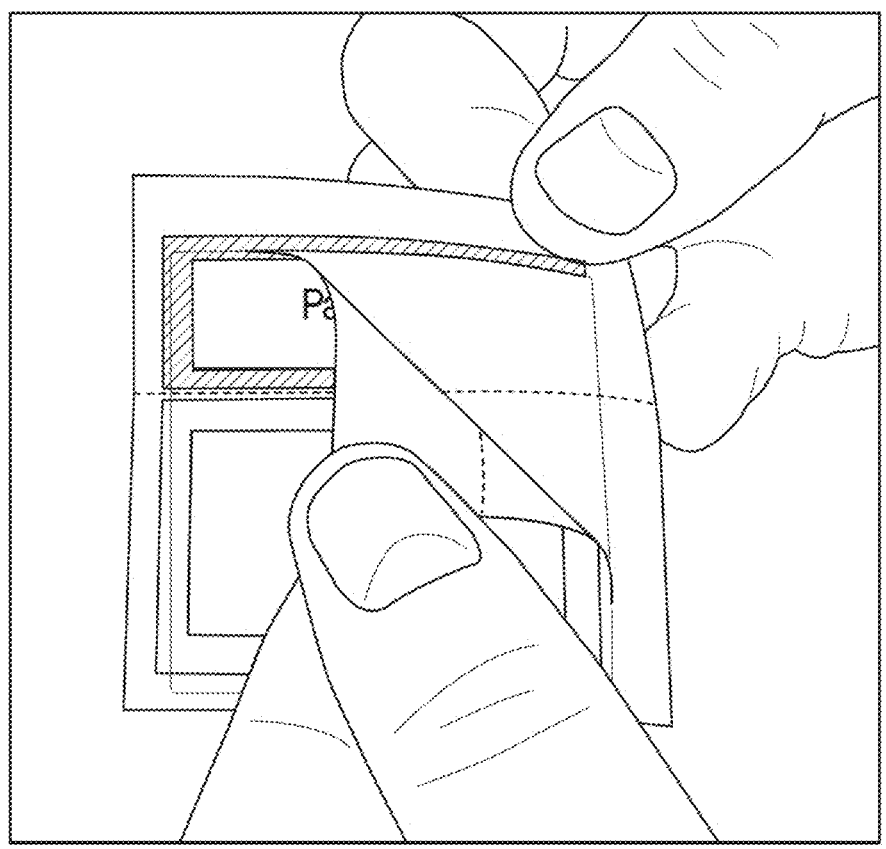
FIG. 3B illustrates a step of applying a transdermal dosing unit to a subject, in accordance with an embodiment of a method of titrating a dose of a transdermal dosing unit as described in the present disclosure.
Figure 3C:
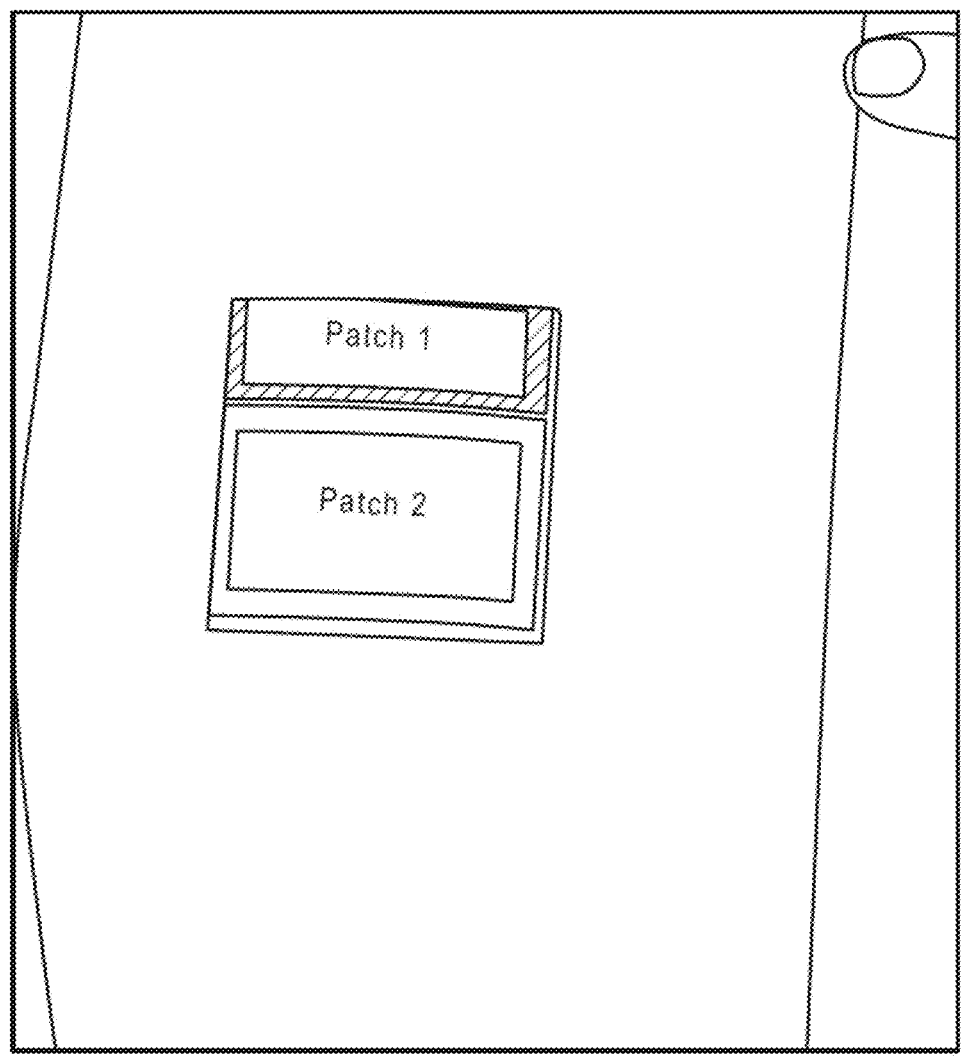
FIG. 3C illustrates a step of applying a transdermal dosing unit to a subject, in accordance with an embodiment of a method of titrating a dose of a transdermal dosing unit as described in the present disclosure.
Figure 3D:
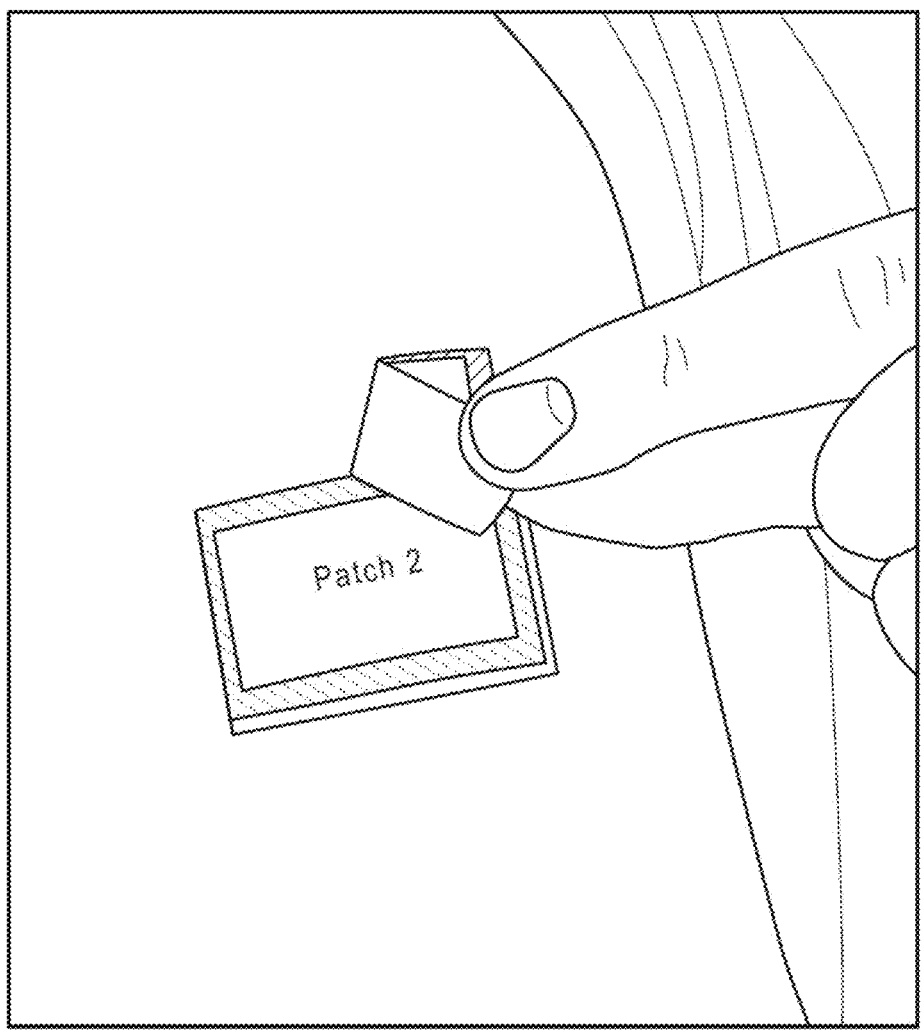
FIG. 3D illustrates a step of removing a first segment of a transdermal dosing unit from a subject while leaving a second segment of the transdermal dosing unit on the subject, in accordance with an embodiment of a method of titrating a dose of a transdermal dosing unit as described in the present disclosure.
Figure 3E:
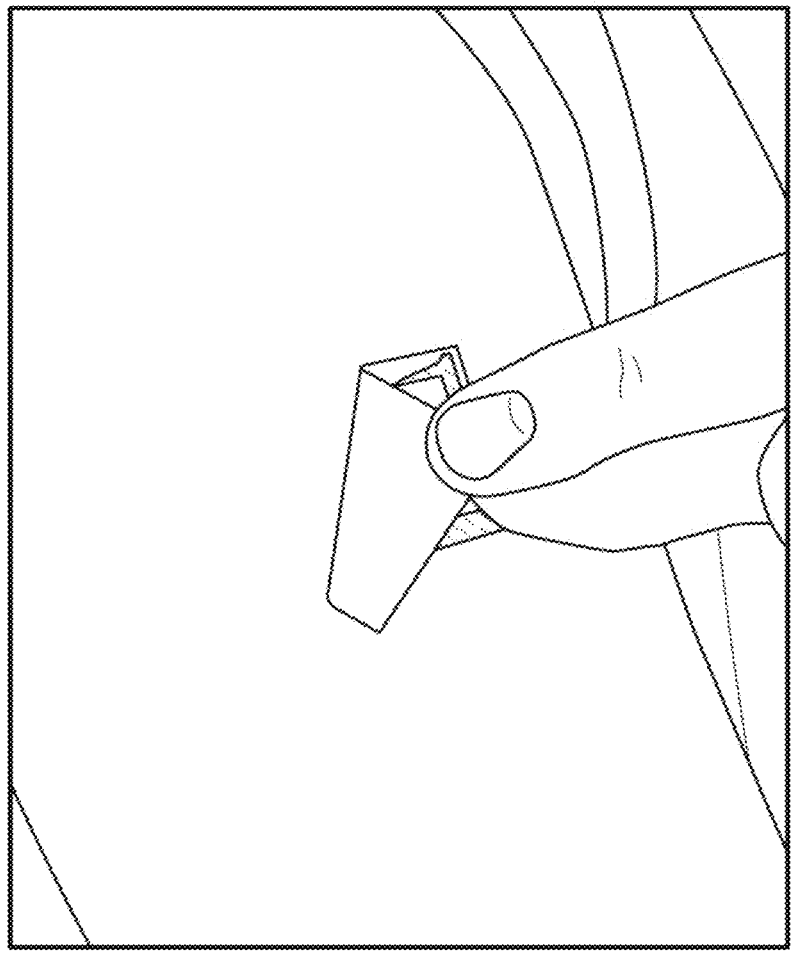
FIG. 3E illustrates a step of removing a second segment of a transdermal dosing unit from a subject after the first segment of the transdermal dosing unit has been removed from the subject, in accordance with an embodiment of a method of titrating a dose of a transdermal dosing unit as described in the present disclosure.
Figure 4A:
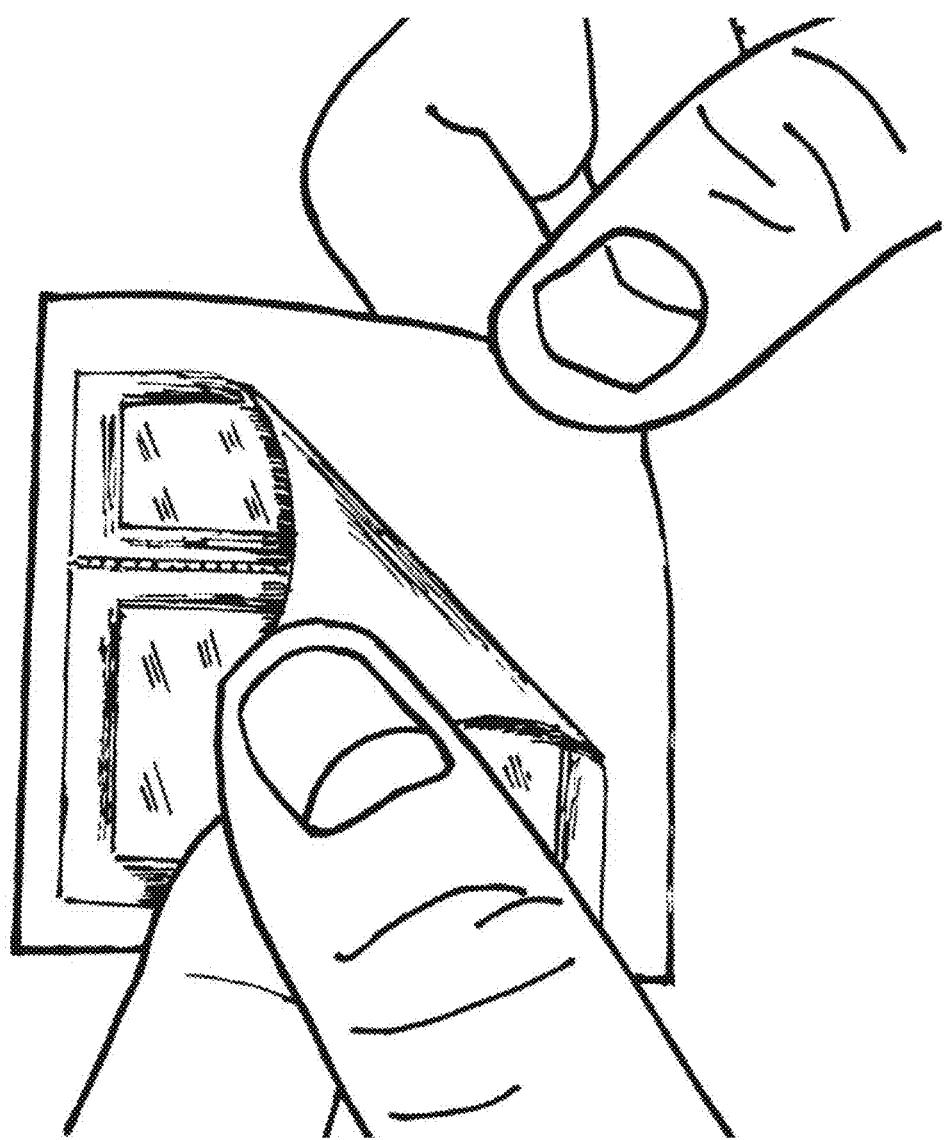
FIG. 4A illustrates a step of applying a transdermal dosing unit to a subject, in accordance with an embodiment of a method of titrating a dose of a transdermal dosing unit as described in the present disclosure.
Figure 4B:
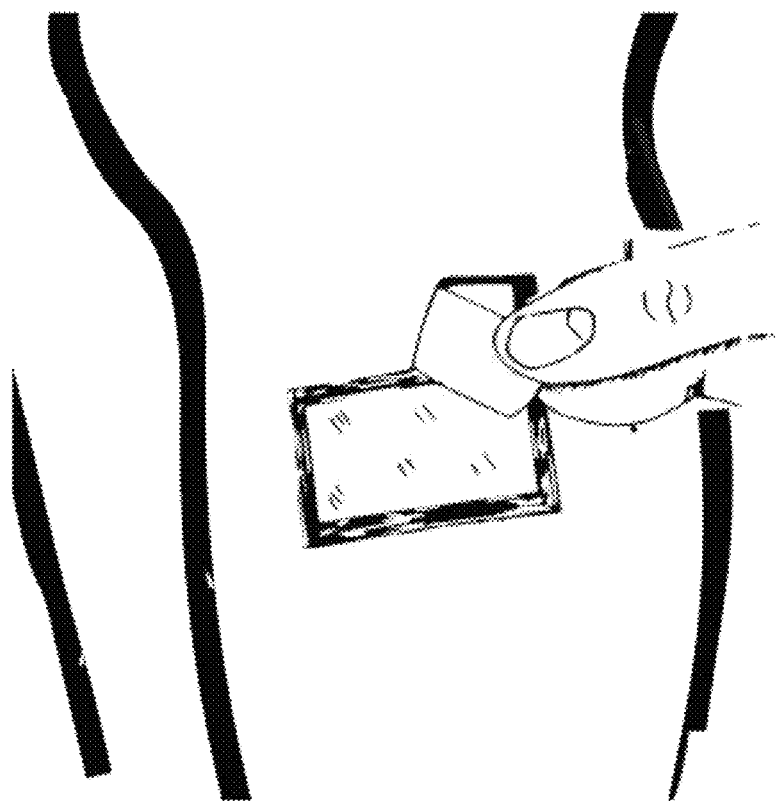
FIG. 4B illustrates a step of removing a first segment of a transdermal dosing unit from a subject while leaving a second segment of the transdermal dosing unit on the subject, in accordance with an embodiment of a method of titrating a dose of a transdermal dosing unit as described in the present disclosure.
Figure 4C:
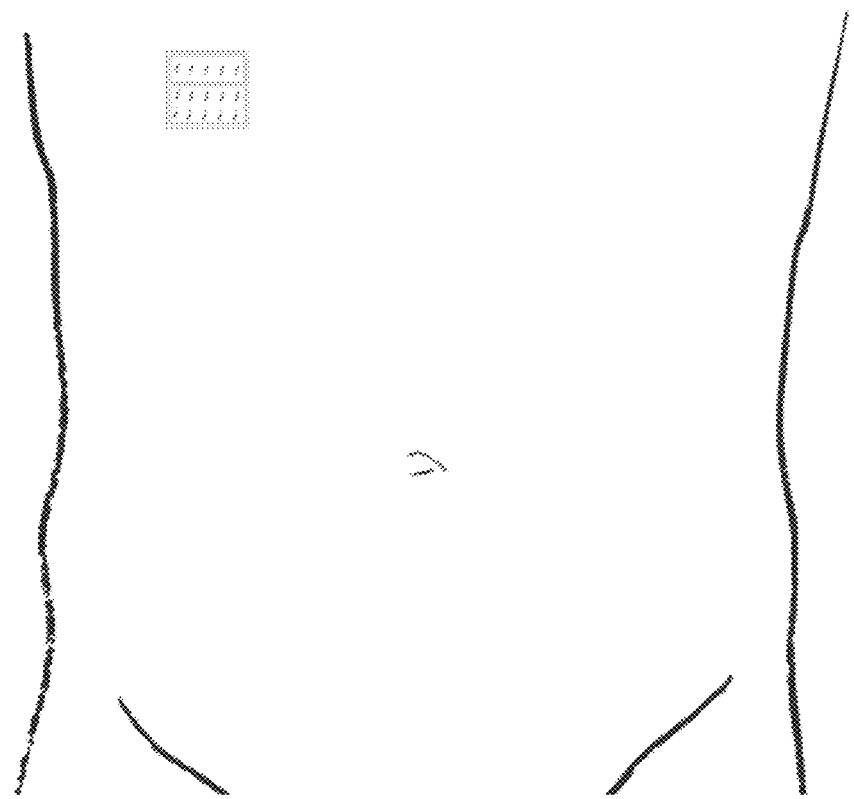
FIG. 4C illustrates a step of applying a transdermal dosing unit to a subject, in accordance with an embodiment of a method of titrating a dose of a transdermal dosing unit as described in the present disclosure.

FIG. 2 illustrates an exemplary embodiment of a transdermal dosing unit, as described herein. As illustrated, the transdermal dosing unit comprises a first segment 100a, a second segment 100b, a backing component 125, and a perforated section 130. The first segment 100a comprises a first reservoir 110a, a first releasing component 115a, and a first adhesive component 120a. The second segment 100b comprises a second reservoir 110b, a second releasing component 115b, and a second adhesive component 120b. In certain embodiments, the first segment 100a may be smaller or have a smaller surface area contacting a subject than the second segment 100b. In other embodiments, the first segment 100a may be larger or have a larger surface area contacting the subject than the second segment 100b. In still other embodiments, the first segment 100a may have a size or surface area contact the subject that may be approximately equal to the second segment 100b.

As described above, each segment of a transdermal dosing unit may comprise one or more reservoirs, which may contain one or more pharmaceuticals. In some embodiments, which may be referred to as "reservoir systems," a reservoir may be embedded between a backing component and a releasing component, which may comprise a rate-controlling membrane. In such embodiments, the pharmaceutical(s) release only through the releasing component, which can be microporous or non-porous. In other embodiments, which may be referred to as "matrix systems," the reservoir may be formed by dispersing the pharmaceutical in an adhesive polymer and spreading that adhesive polymer by solvent casting or by melting the adhesive (in the case of hot-melt adhesives) onto a backing component. Such embodiments may be referred to as "drug-in-adhesive systems." In still other embodiments, which may be referred to as "matrix-dispersion systems," the pharmaceutical may be dispersed homogeneously in a polymer matrix, which may be, for example, hydrophilic or lipophilic. The matrix may be fixed onto an occlusive base plate in a compartment fabricated from a drug-impermeable backing component to form the reservoir. Table 1 illustrates exemplary embodiments of reservoir components in some of the arrangements described above.

TABLE 1

Composition of transdermal delivery systems reported in the literature

| Polymer | Manufacturer | Drug | Type of System |
|---|---|---|---|
| Ethyl cellulose T-50 | Sigma | Isosorbide dinitrate | Matrix |
| BIO PSA HighTack 7-4301 | Dow Corning | Trimegestone | Adhesive-in-matrix system. For matrix |

TABLE 1-continued

Composition of transdermal delivery systems reported in the literature

| Polymer | Manufacturer | Drug | Type of System |
|---|---|---|---|
| BIO PSA MediumTack 7-4201 | | | and backing side layer. |
| Scotch Pak 1022 | 3M | | Backing |
| Scotch Pak 1006 | 3M | | Release liner |
| HPMC | | Hydrocortisone | Gel |
| Eudragit NE, Eudragit E100, Eudragit L100 | Rohm, Germany | Coumarin Melilot dry extract | Matrix |
| MDX-4-421 (a silicone) | Dow Corning | $_L$-Timolol maleate | Matrix |
| Carboxy vinyl polymer | | $_L$-Dopa | Gel |
| Acrylic PSA emulsion | Neoplast Co., Thailand | Nicotine | Drug-in-adhesive |
| CoTran9722 | 3M | | |
| Soybean lecithin (Epikuron 200) | Lucas Meyer, Germany | Scopolamine, broxaterol | Gel matrices |
| Cariflex TR-1107 | Shell Chemical Co., Japan | Dihydro etorphine | Drug-in-adhesive |
| Acrylic adhesives | National Starch and Chemical Co. | Ketoprofen | Drug-in-adhesive |
| Polyisobutylene solutions (Vistanex LM-MH, Vistanex MML-100) | Exxon Chemical Co. | | |
| Acrylic adhesives | National Starch and Chemical Co. | Tacrine | Drug-in-adhesive |
| Polyisobutylene solutions (Vistanex LM-MH, Vistanex MML-100) | Exxon Chemical Co. | | |
| Silicone PSA | | | |
| Silicone oil | Adhesive Research | Arecoline | Reservoir |
| EVA | | | Membrane |
| Polyisobutylene | | | Adhesive |
| ScotchPak 1006 | 3M | | Backing film |
| 2-Ethylhexyl acrylate and acrylic acid copolymer | Mitsubishi Petro-chem Co., Japan Wako Purechem. Ind., Japan | PGE | Drug-in-adhesive matrix |
| HEMA, Styrene and N-vinyl pyrrolidone copolymer for membrane | Polyscience | Cytarabine, ara-ADA | Carbopol 934 gel, reservoir |
| HPMC (Methocel K4M) | Colorcon, UK | Propranolol | Matrix |
| Urecryl MC 808 | UCB, Belgium | | |
| PIB | Aldrich, France | | |
| MDX4-4210 silicone elastomer | Dow Corning | Nitroglycerine | Matrix |
| Acrylate copolymer (Gelva-737) | Monsanto Dow Corning | Fentanyl | Matrix |
| Silicone-2920 and 2675 | Exxon Chemical Co. | | |
| Polyisobutylene solutions (Vistanex LM-MS, Vistanex MML-100) | | | |
| 2-Ethylhexyl acrylate and acrylic acid copolymer | Mitsubishi Petro-chem Co., Japan Wako Purechem. Ind., Japan | Aminopyrene, Ketoprofen, Lidocaine | Drug-in-adhesive |
| 2-Ethylhexyl acrylate and acrylamide copolymer | | | |
| Polyisobutylene solutions (Vistanex LM-MH, Vistanex LM-80) | Exxon Chemical Co. | | |
| Silicone PSA | Dow Corning | | |
| Plastoid E25L | Rohm, Germany | Miconazole | Matrix |
| Polyvinyl alcohol (backing) HPMC (matrix) Ethylene vinyl acetate (rate-controlling membrane) | | Propranolol | Membrane-controlled reservoir system |

Also as described above, each segment of a transdermal dosing unit may comprise one or more releasing components near the one or more reservoirs. Such releasing components may be permeable or semipermeable to the one or more pharmaceuticals contained in the one or more reservoirs, and may be configured to release the one or more pharmaceuticals at one or more controlled rates. In some embodiments, the releasing components may comprise, for example, natural polymers, synthetic elastomers, synthetic polymers, combinations thereof, or derivatives thereof. Natural polymers may include, for example, cellulose derivatives, zein, gelatin, shellac, waxes, gums, natural rubber and chitosan. Synthetic elastomers may include, for example, polybutadiene, hydrin rubber, polyisobutylene, silicon rubber, nitrile, acrylonitrile, neoprene, and butylrubber. Synthetic polymers may include, for example, polyvinyl alcohol, polyvinylchloride, polyethylene, polypropylene, polyacrylate, polyamide, polyurea, polyvinylpyrrolidone, polymethylmethacrylate cross-linked polyethylene glycol, eudragits, ethyl cellulose, polyvinylpyrrolidone, hydroxypropylmethylcellulose, EVA, silicon rubber, and polyurethane. In some embodiments, a releasing component may further comprise one or more layers of a coating, such as silicon or polytetrafluoroethylene, for example.

In some embodiments, each segment of a transdermal dosing unit may independently contain one or more adhesive components. The adhesive components may serve to adhere the segments, or the components of each segment, together. The adhesive components may also serve to adhere the transdermal dosing unit to the subject. Each adhesive component may comprise, for example, an acrylate ester/vinyl pyrrolidone copolymer, a dimethyl silicone polymer, an acrylate polymer, derivatives thereof, and combinations thereof. In some embodiments, an adhesive component may comprise, for example, ethylene vinyl acetate copolymers, paraffin waxes, low-density polypropylene, styrene-butadiene copolymers, ethylene-ethacrylate copolymers, polyesters, polyamides, polyurethanes, combinations thereof, or derivatives thereof.

In some embodiments, the adhesive component(s) of each segment may be the same or similar, while in other embodiments the adhesive component(s) of each segment may differ. In some embodiments, the adhesive component of each segment may comprise one or more adhesion strengths, which may be measured by tensile strength, surface tension, critical surface tension, peel adhesion, shear adhesion, or viscosity, for example. The adhesion strengths of the adhesive components may be the same or similar, or they may differ. In an embodiment, for example, the adhesive strength of the first adhesive component may be greater than the adhesive strength of the second adhesive component. In other embodiments, the adhesive strength of the first adhesive component may be approximately equal to the adhesive strength of the second adhesive component. In still other embodiments, the adhesive strength of the first adhesive component may be less than the adhesive strength of the second adhesive component. In some embodiments, a transdermal dosing unit having one or more segments with different adhesive components having different adhesive strengths may serve to facilitate or ease the removal of one or more segments, while increasing the likelihood that the remaining segment(s) continue to be adhered to the subject.

In some embodiments, the first adhesive component and the second adhesive component may independently comprise, for example, a silicone adhesive. In one non-limiting example, the first adhesion strength of the first adhesive component may be a peel adhesion strength of about 500 g/cm, and the second adhesion strength of the second adhesion component may be a peel adhesion strength of about 900 g/cm. Such a combination would result in an adhesion strength ratio of about 0.56 (500 g/cm:900 g/cm). A wide range of adhesive strength ratios may be used in the embodiments described herein. A first adhesive component may have an adhesion strength ratio to any other adhesive component of, for example, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, or any range between any two of these ratios, including endpoints. In one embodiment, the adhesion strength ratio of the first adhesion strength to the second adhesion strength may be in the range of about 0.6 to about 1.0.

In certain embodiments, the removal of one or more segments may be further facilitated by having different surface areas contacting the patient for different segments of the transdermal dosing unit. In one non-limiting example, the first segment may comprise first adhesive component with a first adhesion strength and a first surface area contacting the patient, while the second segment may comprise a second adhesive component with a second adhesion strength higher than the first adhesion strength, and a second surface area larger than the first surface area contacting the patient. In such an embodiment, the differences in adhesion strengths and surface areas may result in the first segment being easier to remove without disturbing the adhesion of the second segment to the subject.

In some embodiments, each adhesive component may independently have an adhesion strength measured by surface tension from about 1 nN/m to about 40 nN/m. The surface tension may be, for example, about 1 nN/m, about 2 nN/m, about 3 nN/m, about 4 nN/m, about 5 nN/m, about 6 nN/m, about 7 nN/m, about 8 nN/m, about 9 nN/m, about 10 nN/m, about 11 nN/m, about 12 nN/m, about 13 nN/m, about 14 nN/m, about 15 nN/m, about 16 nN/m, about 17 nN/m, about 18 nN/m, about 19 nN/m, about 20 nN/m, about 21 nN/m, about 22 nN/m, about 23 nN/m, about 24 nN/m, about 25 nN/m, about 26 nN/m, about 27 nN/m, about 28 nN/m, about 29 nN/m, about 30 nN/m, about 31 nN/m, about 32 nN/m, about 33 nN/m, about 34 nN/m, about 35 nN/m, about 36 nN/m, about 37 nN/m, about 38 nN/m, about 39 nN/m, about 40 nN/m, or any range between any of these values, including endpoints.

In some embodiments, each adhesive component may independently have an adhesion strength measured by critical surface tension from about 1 mN/m to about 50 mN/m. The critical surface tension may be, for example, about 1 mN/m, about 2 mN/m, about 3 mN/m, about 4 mN/m, about 5 mN/m, about 6 mN/m, about 7 mN/m, about 8 mN/m, about 9 mN/m, about 10 mN/m, about 11 mN/m, about 12 mN/m, about 13 mN/m, about 14 mN/m, about 15 mN/m, about 16 mN/m, about 17 mN/m, about 18 mN/m, about 19 mN/m, about 20 mN/m, about 21 mN/m, about 22 mN/m, about 23 mN/m, about 24 mN/m, about 25 mN/m, about 26 mN/m, about 27 mN/m, about 28 mN/m, about 29 mN/m, about 30 mN/m, about 31 mN/m, about 32 mN/m, about 33 mN/m, about 34 mN/m, about 35 mN/m, about 36 mN/m, about 37 mN/m, about 38 mN/m, about 39 mN/m, about 40 mN/m, about 41 mN/m, about 42 mN/m, about 43 mN/m, about 44 mN/m, about 45 mN/m, about 46 mN/m, about 47 mN/m, about 48 mN/m, about 49 mN/m, about 50 mN/m, or any range between any of these values, including endpoints.

In some embodiments, each adhesive component may independently have an adhesion strength measured by peel adhesion from about 100 g/cm to about 1500 g/cm. The peel adhesion may be, for example, about 100 g/cm, about 150 g/cm, about 200 g/cm, about 250 g/cm, about 300 g/cm, about 350 g/cm, about 400 g/cm, about 450 g/cm, about 500 g/cm, about 550 g/cm, about 600 g/cm, about 650 g/cm, about 700 g/cm, about 750 g/cm, about 800 g/cm, about 850 g/cm, about 900 g/cm, about 950 g/cm, about 1000 g/cm, about 1050 g/cm, about 1100 g/cm, about 1150 g/cm, about 1200 g/cm, about 1250 g/cm, about 1300 g/cm, about 1350 g/cm, about 1400 g/cm, about 1450 g/cm, about 1500 g/cm, or any range between any of these values, including endpoints.

In certain embodiments, the first adhesive component and the second adhesive component may be removably connected by one or more perforations, as described above. Such a perforation may create a boundary condition, which may allow the composition of the first adhesive component to differ from the composition of the second adhesive component.

Table 2, Table 3, Table 4, and Table 5 below illustrate exemplary embodiments of various possible adhesive components and adhesion strengths thereof.

TABLE 2

| Thermoplastic hot-melt pressure-sensitive adhesives |
| --- |
| Compounded |
| Ethylene vinyl acetate copolymers |
| Paraffin waxes |
| Low-density polypropylene |
| Styrene-butadiene copolymers |
| Ethylene-ethacrylate copolymers |
| Uncompounded |
| Polyesters |
| Polyamides |
| Polyurethanes |

TABLE 3

| Polymer | Critical Surface tension @ 20° C. mNm$^{-1}$ (dyn cm$^{-1}$) | Surface Tension (temp. of measurement) nNm$^{-1}$ (dyn cm$^{-1}$) | How measured |
| --- | --- | --- | --- |
| Polytetrafluoroethylene (Teflon ®) | 18 | 9.4 (180° C.) | Wilhemy plate |
| High density polyethylene | 31 | 26.5 (180° C.) | Pendent drop |
| Polyethylene terephthalate | 43 | 27.0 (290° C.) | Rotating bubble |
| Poly vinyl alcohol | 37 | N/A | |
| Poly vinyl chloride | 40 | N/A | |

TABLE 4

| Adhesive | Critical surface tension mNm$^{-1}$ (dyn cm$^{-1}$) | How measured |
| --- | --- | --- |
| Poly (dimethyl siloxane) PSA | 22 | Advancing & receding angles |
| Polyacrylate PSA | 27-42[a] | Rame-Hart contact angle |
| Polyisobutylene (PIB + polybutene) (PB) PSA | 30-32 | Advancing & receding angles |

[a]The values are for a copolymer of n-butyl acrylate and acrylic acid, with values increasing as AA content.

TABLE 5

| Adhesive type | Peel adhesion, stainless steel g cm$^{-1}$ | Polyken tack, (0.5 cm probe), g | Thickness |
| --- | --- | --- | --- |
| PIB binary blend[a] | 300-700 | 1000-1400 | 3 mil |
| PIB + PB[b] | 910 | 370-800 | 2.5 mil |
| PIB + PB + Tackifier[c] | 750-1200 | 1400-1900 | 4 mil |

All values measured at ALZA Corporation; where range is given, several lots were measured.
[a]High-MW PIB:low-MW PIB is approximately 15:85.
[b]Approximately 1:5:2 ratio of high-MW PIB:low-MW PIB:PB
[c]Adhesives Research Inc. product.

As described above, a transdermal dosing unit may also comprise a backing component. The backing component may serve to protect each segment from the environment. In some embodiments, the backing component may be non-permeable to pharmaceuticals and other environmental factors, including moisture. In some embodiments, the backing component may exhibit a low modulus and/or a high flexibility, good oxygen transmission, and/or a high moisture vapor transmission rate. A backing component may comprise, for example, vinyl, polyethylene, a polyester film, combinations thereof, or derivatives thereof. In some embodiments, each segment of the transdermal dosing unit may share a common backing. The common backing may serve to connect each segment into a single unit. In other embodiments, the common backing may be perforated to allow the subject or a healthcare professional to remove one or more segments while leaving one or more segments adhered to the subject. Table 6 below illustrates exemplary embodiments of backing components.

TABLE 6

Characteristics of some commercialized backing materials

| Product | Polymer | Oxygen Transmission ($cm^3/m^2/24$ h) | MVTR ($g/m^2/24$ h) | Enhancer Resistance |
|---|---|---|---|---|
| CoTran 9701 | Polyurethane film | | 700 | Low |
| CoTran 9702 | EVA | | 52.8 | Medium |
| CoTran 9706 | | | 26.4 | Medium |
| CoTran 9720 | PE | 2950 | 9.4 | Medium |
| CoTran 9722 | | 3570 | 7.9 | High |
| Foam Tape 9772L | PVC foam | | 450 | — |
| Foam Tape 9773 | Polyolefin foam | | — | — |
| Scotchpak 1006 | PE, Al vapor coat, PET, EVA | 4.6 | 0.3 | High-PET side |
| Scotchpak 1109 | PE, Al vapor coat, PET | 4.6 | 0.3 | High |
| Scotchpak 9723 | PE, PET laminate | 100 | 12 | High-PET side |
| Scotchpak 9732, 9733 | PET, EVA laminate | 80 | 15.5 | High-PET side |
| | | 80 | 17 | |

Oxygen
PE = Polyethylene
PVC = Polyvinyl chloride
EVA = Ethylene vinyl acetate
MVTR = Moisture-vapor transmission rate
PP = Polypropylene
PU = Polyurethane
PET = Poly(ethylene terephthalate) (polyester)

Each segment of a transdermal dosing unit may independently comprise one or more pharmaceuticals. In some embodiments, a transdermal dosing unit may include two or more segments, wherein each segment independently comprises a pharmaceutical as described herein. In one embodiment, the two or more segments may each comprise a different pharmaceutical, while in other embodiments, the two or more segments may comprise the same pharmaceutical. In some embodiments, the two or more segments may comprise the same pharmaceutical, and the amount of pharmaceutical in each segment may be the same, different, or a combination thereof. In some embodiments, the pharmaceutical may comprise, for example, a solution, suspension, or a gel, or may be dispersed in a solid polymer matrix. In some embodiments, each segment may further comprise a pharmaceutically acceptable carrier, diluent, or excipient. For example, the transdermal dosing unit may comprise a first segment comprising a first pharmaceutical and a second segment comprising the same pharmaceutical, wherein the pharmaceutical may be present in each segment in the same or in different dose amounts. In an embodiment, the pharmaceutical may be contained in one or more reservoirs, and may be in direct contact with one or more releasing components. In some embodiments, the transdermal dosing unit may comprise a first segment comprising a first pharmaceutical and a second segment comprising a second pharmaceutical. In other embodiments, the transdermal dosing unit may further comprise, for example, a third segment comprising a third pharmaceutical, a fourth segment comprising a fourth pharmaceutical, a fifth segment comprising a fifth pharmaceutical, a sixth segment comprising a sixth pharmaceutical, a seventh segment comprising a seventh pharmaceutical, an eighth segment comprising an eighth pharmaceutical, and so on, wherein each pharmaceutical is selected independently from the other pharmaceutical(s).

In some embodiments, each pharmaceutical may be independently selected from, for example, methylphenidate, clonidine, fentanyl, fentanyl intophoretic, rivastigmine, selegiline, lidocaine, buprenorphine, scopolamine, estradiol, estradiol/levonorgestrel, estradiol/norethindrone acetate, granisetron, nicotine, nitroglycerin, norelgestromin/ethinyl estradiol, oxybutynin, rotigotine, testosterone, prednisone, derivatives thereof, or combinations thereof.

In some embodiments, the pharmaceutical may comprise methylphenidate in an amount of about 1 mg to about 40 mg. The amount of methylphenidate may be, in some non-limiting examples, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, or any range between any two of these values, including endpoints.

In some embodiments, the pharmaceutical may comprise clonidine in an amount of about 0.1 mg to about 1.0 mg. The amount of clonidine may be, in some non-limiting examples, about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, or any range between any two of these values, including endpoints.

In some embodiments, the pharmaceutical may comprise fentanyl in an amount of about 1 μg to about 150 μg. The amount of fentanyl may be, in some non-limiting examples, about 1 μg, about 5 μg, about 10 μg, about 11 μg, about 12 μg, about 13 μg, about 14 μg, about 15 μg, about 20 μg, about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 105 μg, about 110 μg, about 115 μg, about 120 μg, about 125 μg, about 130 μg, about 135 μg, about 140 μg, about 145 μg, about 150 μg, or any range between any two of these values, including endpoints.

In some embodiments, the pharmaceutical may comprise fentanyl intophoretic in an amount of about 1 µg to about 100 µg. The amount of fentanyl intophoretic may be, in some non-limiting examples, about 1 µg, about 5 µg, about 10 µg, about 11 µg, about 12 µg, about 13 µg, about 14 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, or any range between any two of these values, including endpoints.

In some embodiments, the pharmaceutical may comprise rivastigmine in an amount of about 1 µg to about 20 µg. In other embodiments, the pharmaceutical may comprise rivastigmine in an amount of about 4.6 µg to about 13.3 µg. The amount of rivastigmine may be, in some non-limiting examples, about 1 µg, about 2 µg, about 3 µg, about 4 µg, about 4.6 µg, about 5 µg, about 6 µg, about 7 µg, about 8 µg, about 9 µg, about 10 µg, about 11 µg, about 12 µg, about 13 µg, about 13.3 µg, about 14 µg, about 15 µg, about 16 µg, about 17 µg, about 18 µg, about 19 µg, about 20 µg, or any range between any two of these values, including endpoints.

In some embodiments, the pharmaceutical may comprise buprenorphine in an amount of about 1 µg to about 30 µg. The amount of buprenorphine may be, in some non-limiting examples, about 1 µg, about 5 µg, about 10 µg, about 11 µg, about 12 µg, about 13 µg, about 14 µg, about 15 µg, about 20 µg, about 25 µg, about 30 µg, or any range between any two of these values, including endpoints.

In some embodiments, the pharmaceutical may comprise selegiline in an amount of about 1 mg to about 20 mg. The amount of selegiline may be, in some non-limiting examples, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, or any range between any two of these values, including endpoints.

In some embodiments, the pharmaceutical may comprise lidocaine in a percent concentration from about 0.1% to about 20%. The percent concentration of lidocaine may be, in some non-limiting examples, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or any range between any two of these values, including endpoints.

In some embodiments, the pharmaceutical may comprise scopolamine in an amount of about 0.1 mg to about 5 mg. The amount of scopolamine may be, in some non-limiting examples, about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.5 mg, about 4.0 mg, about 4.5 mg, about 5.0 mg, or any range between any two of these values, including endpoints.

In some embodiments, the pharmaceutical may comprise estradiol in an amount of about 0.001 mg to about 5 mg. The amount of estradiol may be, in some non-limiting examples, about 0.001 mg, about 0.025 mg, about 0.0375 mg, about 0.05 mg, about 0.06 mg, about 0.075 mg, 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.5 mg, about 4.0 mg, about 4.5 mg, about 5.0 mg, or any range between any two of these values, including endpoints.

In some embodiments, the pharmaceutical may comprise estradiol/levonorgestrel in an amount of about 0.001 mg to about 5 mg. The amount of estradiol/levonorgestrel may be, in some non-limiting examples, about 0.001 mg, about 0.015 mg, about 0.025 mg, about 0.0375 mg, about 0.045 mg, about 0.05 mg, about 0.06 mg, about 0.075 mg, 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.5 mg, about 4.0 mg, about 4.5 mg, about 5.0 mg, or any range between any two of these values, including endpoints.

In some embodiments, the pharmaceutical may comprise estradiol/norethindrone acetate in an amount of about 0.001 mg to about 5 mg. The amount of estradiol/norethindrone acetate may be, in some non-limiting examples, about 0.001 mg, about 0.014 mg, about 0.015 mg, about 0.025 mg, about 0.0375 mg, about 0.045 mg, about 0.05 mg, about 0.06 mg, about 0.075 mg, 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.5 mg, about 4.0 mg, about 4.5 mg, about 5.0 mg, or any range between any two of these values, including endpoints.

In some embodiments, the pharmaceutical may comprise granisetron in an amount of about 0.1 mg to about 5 mg. The amount of granisetron may be, in some non-limiting examples, about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.1 mg, about 3.5 mg, about 4.0 mg, about 4.5 mg, about 5.0 mg, or any range between any two of these values, including endpoints.

In some embodiments, the pharmaceutical may comprise nicotine in an amount of about 1 mg to about 40 mg. The amount of nicotine may be, in some non-limiting examples, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, or any range between any two of these values, including endpoints.

In some embodiments, the pharmaceutical may comprise nitroglycerin in an amount of about 0.1 mg to about 5 mg. The amount of nitroglycerin may be, in some non-limiting examples, about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.1 mg, about 3.5 mg, about 4.0 mg, about 4.5 mg, about 5.0 mg, or any range between any two of these values, including endpoints.

In some embodiments, the pharmaceutical may comprise norelgestromin/ethinyl estradiol in an amount of about 1 µg to about 200 µg. The amount of norelgestromin/ethinyl estradiol may be, in some non-limiting examples, about 1 µg, about 5 µg, about 10 µg, about 11 µg, about 12 µg, about 13 µg, about 14 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 105 µg, about 110 µg, about 115 µg, about 120 µg, about 125 µg, about 130 µg, about 135 µg, about 140 µg, about 145 µg, about 150 µg, about 155 µg, about 160 µg, about 165 µg, about 170 µg, about 175 µg, about 180 µg, about 185 µg, about 190 µg, about 195 µg, about 200 µg, or any range between any two of these values, including endpoints.

In some embodiments, the pharmaceutical may comprise oxybutynin in an amount of about 0.1 mg to about 5 mg. The amount of nitroglycerin may be, in some non-limiting examples, about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.1 mg, about 3.5 mg, about 3.9 mg, about 4.0 mg, about 4.5 mg, about 5.0 mg, or any range between any two of these values, including endpoints.

In some embodiments, the pharmaceutical may comprise rotigotine in an amount of about 1 mg to about 20 mg. The amount of rotigotine may be, in some non-limiting examples, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, or any range between any two of these values, including endpoints.

In some embodiments, the pharmaceutical may comprise testosterone in an amount of about 0.1 mg to about 5 mg. The amount of testosterone may be, in some non-limiting examples, about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.1 mg, about 3.5 mg, about 3.9 mg, about 4.0 mg, about 4.5 mg, about 5.0 mg, or any range between any two of these values, including endpoints.

In one embodiment, the first pharmaceutical of the transdermal dosing unit may comprise methylphenidate, and the second pharmaceutical may comprise selegiline. In some embodiments, such combinations may be used in the treatment of, for example, depression, attention-deficit disorder, attention-deficit/hyperactivity disorder, or a combination thereof.

In another embodiment, the first pharmaceutical of the transdermal dosing unit may comprise lidocaine, and the second pharmaceutical may comprise fentanyl. In yet another embodiment, the first pharmaceutical of the transdermal dosing unit may comprise lidocaine, and the second pharmaceutical may comprise buprenorphine. In some embodiments, such combinations may be used in the treatment of, for example, acute pain, chronic pain, or a combination thereof.

In still other embodiments, the first pharmaceutical of the transdermal dosing unit may comprise lidocaine, fentanyl, buprenorphine, or a combination thereof, and the second pharmaceutical may comprise scopolamine. In some embodiments, such combinations may be used in the treatment of, for example, acute pain, chronic pain, respiratory secretions, or a combination thereof.

In some embodiments, the first pharmaceutical of the transdermal dosing unit may comprise selegiline, and the second pharmaceutical may comprise lidocaine. In some embodiments, such a combination may be used in the treatment of, for example, fibromyalgia.

In other embodiments, the first pharmaceutical of the transdermal dosing unit may comprise buprenorphine, and the second pharmaceutical may comprise clonidine. In some embodiments, such a combination may be used in the treatment of, for example, opiate substance abuse.

Methods of Titrating a Dose of a Transdermal Dosing Unit

Figure 5A:
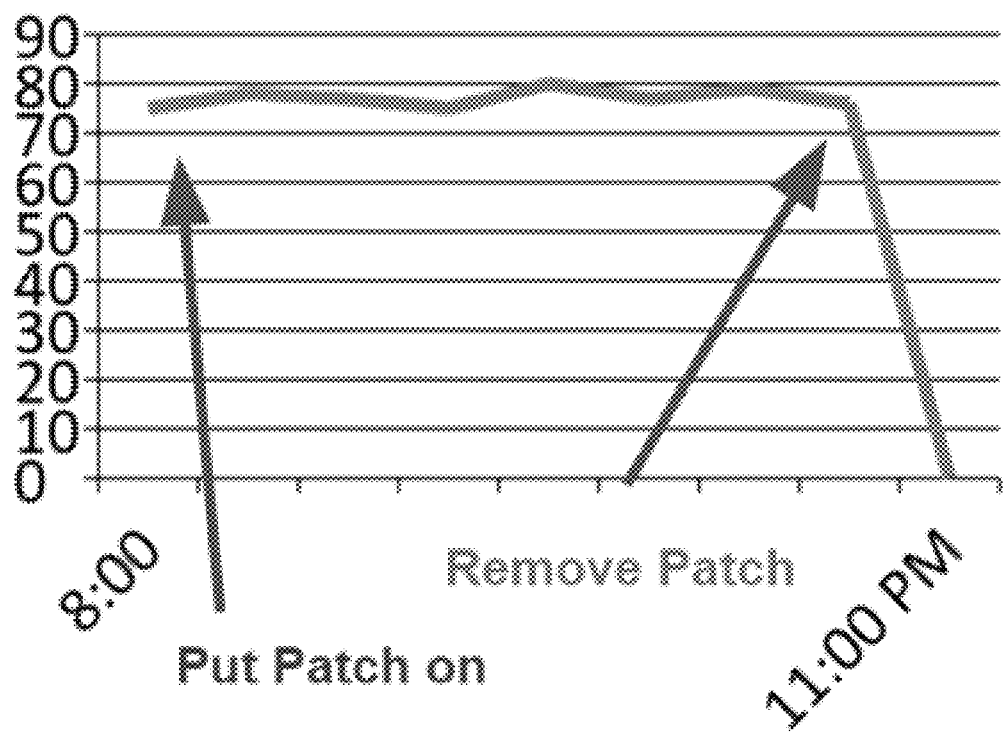
FIG. 5A is a graphical representation of a dose timeline of a transdermal dosing unit having a single segment.
Figure 5B:
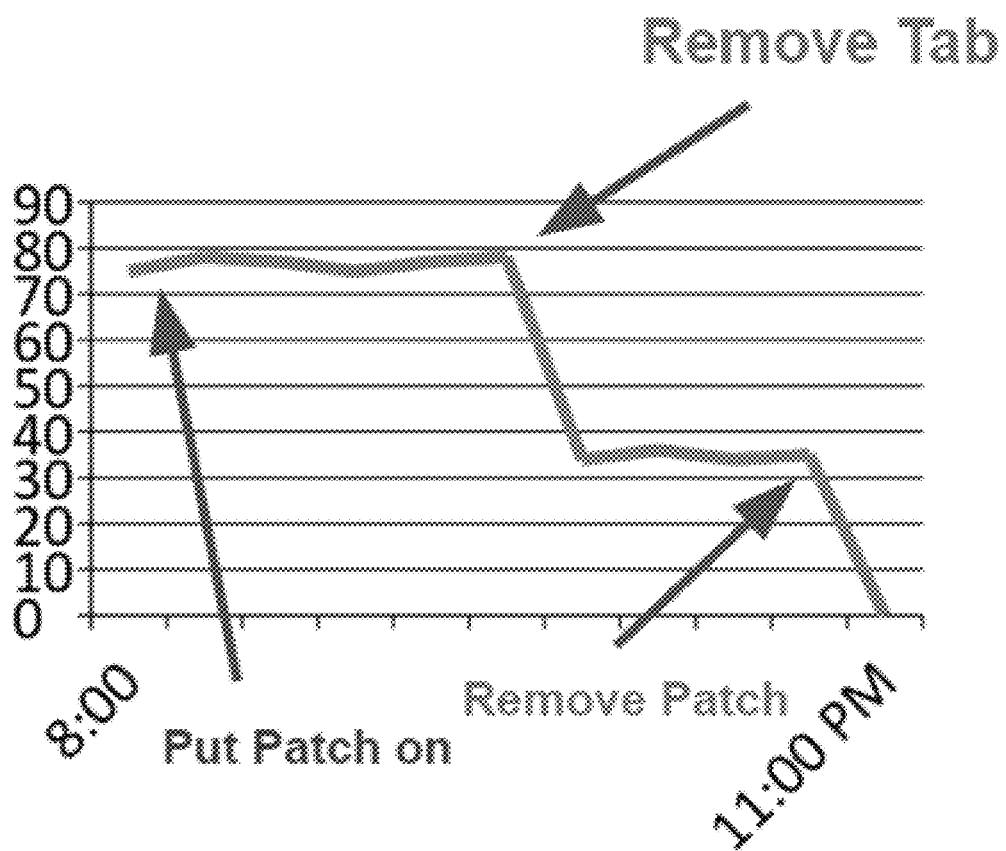
FIG. 5B is a graphical representation of a dose timeline of a transdermal dosing unit having an additional removable segment, in accordance with the present disclosure.

In an embodiment, a method of titrating a dose of a transdermal dosing unit may comprise applying to a subject a transdermal dosing unit as described herein, and removing at least one segment of the transdermal dosing unit while leaving one or more segments of the transdermal dosing unit on, or adhered to, the subject. In another embodiment, a method of titrating a dose of a transdermal dosing unit may comprise applying to a subject a transdermal dosing unit as described herein, and leaving the entire transdermal dosing unit on, or adhered to, the subject, for a prescribed amount of time. In some embodiments, the method may comprise applying a transdermal dosing unit having a first segment and a second segment, as described herein, and removing the first segment while leaving the second segment on, or adhered to, the subject. In some embodiments, the two or more segments may comprise the same pharmaceutical, the amount of pharmaceutical in each segment may be the same, different, of a combination thereof. FIG. 3A, FIG. 3B, FIG. 3C, FIG. 3D, FIG. 3E, FIG. 4A, FIG. 4B, and FIG. 4C illustrate embodiments of methods of titrating a dose of a transdermal dosing unit, in accordance with the present disclosure. FIG. 5A and FIG. 5B are graphical representations of a dose timeline of a transdermal dosing unit having a single segment and an additional removable segment, respectively, in accordance with the present disclosure. FIG. 5B, in particular, illustrates an embodiment of a method of titrating a dose of a transdermal unit, as described herein. In FIG. 5B, one of ordinary skill in the art would appreciate the full dose of medication when the transdermal dosing unit is initially applied, the partial decrease in dosage after a first segment is removed, and the further decrease in dosage after the remaining segment(s) are removed.

In certain embodiments, a method of titrating a dose may include applying a transdermal dosing unit as described herein, and removing one or more segments of the transdermal dosing unit over a pre-planned period of time in order to gradually decrease the dose of the pharmaceutical(s) the subject receives. In some embodiments, for example, the first pharmaceutical and the second pharmaceutical of the transdermal dosing unit (and optionally, any additional pharmaceuticals of additional segments) may comprise prednisone; in such an embodiment, a method of titrating the dose of prednisone may include applying the transdermal dosing unit to the subject, and removing the first segment (and optionally, the additional segments) at prescribed times in order to taper the dose of prednisone the subject receives. Similar embodiments may be envisioned for any orally or parenterally administered drugs that may be subject to a tapering protocol or prescription.

In other embodiments, a method of titrating a dose may include applying a transdermal dosing unit as described herein, and removing the first segment of the transdermal dosing unit once the subject has received a sufficient initial dose, or "loading" dose, but leaving the second segment on the subject to continue to deliver a continuous dose, or "maintenance" dose. Similar embodiments may be envisioned for any orally or parenterally administered drugs that may be subject to a loading and maintenance dose protocol or prescription.

In certain embodiments, the first and second segments of the transdermal dosing unit may comprise a first pharmaceutical that is different from the second pharmaceutical; a method of titrating a dose using such a transdermal dosing unit may comprise applying the transdermal dosing unit as described herein in order to deliver both the first pharmaceutical and the second pharmaceutical to the subject, and later removing the first segment in order to discontinue the subject's exposure to the first pharmaceutical, while leaving the second segment on the subject in order to continue the subject's exposure to the second pharmaceutical. In an embodiment, for example, the first pharmaceutical may comprise clonidine, and the second pharmaceutical may comprise buprenorphine.

As discussed above, in some embodiments, the first pharmaceutical of the transdermal dosing unit may comprise methylphenidate, and the second pharmaceutical may comprise selegiline. In some embodiments, such a combination may be used in the treatment of, for example, depression, attention-deficit disorder, attention-deficit/hyperactivity disorder, or a combination thereof. A method of titrating the dose of such a transdermal dosing unit may comprise, in some examples, applying the transdermal dosing unit to a subject in the morning, removing either the first segment or the second segment during the afternoon, and removing the remaining segment(s) in the evening before the subject goes to sleep. Such a method may be used, for example, to mirror commonly accepted oral dosing regimens while improving known side effects such as lack of appetite and insomnia.

Also as discussed above, in some embodiments, the first pharmaceutical of the transdermal dosing unit may comprise lidocaine, and the second pharmaceutical may comprise fentanyl. In yet another embodiment, the first pharmaceutical of the transdermal dosing unit may comprise lidocaine, and the second pharmaceutical may comprise buprenorphine. In some embodiments, such a combination may be used in the treatment of, for example, acute pain, chronic pain, or a combination thereof. In still other embodiments, the first pharmaceutical of the transdermal dosing unit may comprise lidocaine, fentanyl, buprenorphine, or a combination thereof, and the second pharmaceutical may comprise scopolamine. In some embodiments, such a combination may be used in the treatment of, for example, acute pain, chronic pain, respiratory secretions, or a combination thereof. A method of titrating a dose of a transdermal dosing unit as described in these exemplary embodiments may comprise applying the transdermal dosing unit to the subject, and removing one or more segments of the side effects of the pharmaceuticals become too severe, or if the subject exhibits signs of an overdose. Such a method would allow the level of the pharmaceutical(s) in the subject's blood to be decreased without being completely removed, thereby preventing insufficient pain management or withdrawal symptoms.

In certain embodiments, the method of titrating a dose of a transdermal dosing unit may also include allowing a period of time from about 1 hour to about 7 days to pass between applying the transdermal dosing unit and removing the first segment of the transdermal dosing unit. In some embodiments, for example, the period of time may be about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1.25 days, about 1.5 days, about 1.75 days, about 2 days, about 2.25 days, about 2.5 days, about 2.75 days, about 3 days, about 3.25 days, about 3.5 days, about 3.75 days, about 4 days, about 4.25 days, about 4.5 days, about 4.75 days, about 5 days, about 5.25 days, about 5.5 days, about 5.75 days, about 6 days, about 6.25 days, about 6.5 days, about 6.75 days, about 7 days, or any range between any two of these values, including endpoints.

In some embodiments, the transdermal dosing unit as described herein may comprise an amount of a pharmaceutical sufficient to deliver an effective dose to a subject over the course of an entire month. In other embodiments, the transdermal dosing unit may comprise an amount of a pharmaceutical sufficient to deliver an effective dose to a subject over the course of an entire week.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicants' general inventive concept.

The invention claimed is:

1. A transdermal dosing unit comprising:
   a first segment comprising a first pharmaceutical in a first reservoir, a first releasing component, and a first adhesive component;
   a second segment removably connected to the first segment, the second segment comprising a second pharmaceutical in a second reservoir, a second releasing component, and a second adhesive component; and
   a backing component;
   wherein the first adhesive component comprises a first adhesion strength, wherein the second adhesive component comprises a second adhesion strength different from the first adhesion strength, and wherein an adhesion strength ratio of the first adhesion strength to the second adhesion strength is from about 0.6 to about 0.9.

2. The transdermal dosing unit of claim 1, further comprising a third segment removably connected to at least the second segment, the third segment comprising a third pharmaceutical in a third reservoir, a third releasing component, and a third adhesive component.

3. The transdermal dosing unit of claim 1, further comprising a perforated section between the first segment and the second segment.

4. The transdermal dosing unit of claim 1, wherein the first pharmaceutical and the second pharmaceutical are independently selected from the group consisting of methylphenidate, clonidine, fentanyl, rivastigmine, selegiline, lidocaine, buprenorphine, scopolamine, prednisone, derivatives thereof, and combinations thereof.

5. The transdermal dosing unit of claim 1, wherein the first pharmaceutical comprises methylphenidate in an amount of about 10 mg to about 30 mg.

6. The transdermal dosing unit of claim 1, wherein the first pharmaceutical comprises clonidine in an amount of about 0.1 mg to about 0.6 mg.

7. The transdermal dosing unit of claim 1, wherein the first pharmaceutical comprises fentanyl in an amount of about 12 µg to about 100 µg.

8. The transdermal dosing unit of claim 1, wherein the first pharmaceutical comprises rivastigmine in an amount of about 4.6 mg to about 13.3 mg.

9. The transdermal dosing unit of claim 1, wherein the first pharmaceutical comprises buprenorphine in an amount of about 5 µg to about 20 µg.

10. The transdermal dosing unit of claim 5, wherein the second pharmaceutical comprises selegiline in an amount of about 6 mg to about 12 mg.

11. The transdermal dosing unit of claim 7, wherein the second pharmaceutical comprises lidocaine in a percent concentration from about 1% to about 10%.

12. The transdermal dosing unit of claim 9, wherein the second pharmaceutical comprises lidocaine in a percent concentration from about 1% to about 10%.

13. The transdermal dosing unit of claim 9, wherein the second pharmaceutical comprises clonidine in an amount of about 0.1 mg to about 0.3 mg.

14. The transdermal dosing unit of claim 1, wherein the first pharmaceutical comprises scopolamine in an amount of about 1 mg to about 3 mg.

15. The transdermal dosing unit of claim 1, wherein the first adhesive and the second adhesive are independently selected from the group consisting of an acrylate ester/vinyl pyrrolidone copolymer, a dimethyl silicone polymer, an acrylate polymer, an ethylene vinyl acetate copolymer, a paraffin wax, a low-density polypropylene, a styrene-butadiene copolymer, an ethylene-ethacrylate copolymer, a polyester, a polyamide, a polyurethane, combinations thereof, and derivatives thereof.

16. A method of titrating a dose of a transdermal dosing unit, the method comprising:
applying to a subject a transdermal dosing unit comprising:
a first segment comprising a first pharmaceutical in a first reservoir, a first releasing component, and a first adhesive component;
a second segment removably connected to the first segment, the second segment comprising a second pharmaceutical in a second reservoir, a second releasing component, and a second adhesive component; and
a backing component;
wherein the first adhesive component comprises a first adhesion strength, wherein the second adhesive component comprises a second adhesion strength different from the first adhesion strength, and wherein an adhesion strength ratio of the first adhesion strength to the second adhesion strength is from about 0.6 to about 0.9; and
removing the first segment while leaving the second segment on the subject.

17. The method of claim 16, wherein the transdermal dosing unit further comprises a perforated section between the first segment and the second segment.

18. The method of claim 16, wherein the first pharmaceutical and the second pharmaceutical are independently selected from the group consisting of methylphenidate, clonidine, fentanyl, rivastigmine, selegiline, lidocaine, buprenorphine, scopolamine, derivatives thereof, and combinations thereof.

19. The method of claim 16, wherein the transdermal dosing unit further comprises a third segment removably connected to at least the second segment, the third segment comprising a third pharmaceutical in a third reservoir, a third releasing component, and a third adhesive component, and wherein the method further comprises removing the third segment.

20. The method of claim 19, further comprising removing the third segment from the subject while leaving the second segment on the subject.

21. The method of claim 16, further comprising allowing a period of time from about 1 hour to about 7 days to pass between applying the transdermal dosing unit and removing the first segment of the transdermal dosing unit.

22. The transdermal dosing unit of claim 1, wherein the first segment has a first surface area configured to contact a patient, wherein the second segment has a second surface area configured to contact the patient, and where the first surface area is different from the second surface area.

* * * * *